United States Patent
Bengtsson et al.

(10) Patent No.: US 10,512,730 B2
(45) Date of Patent: Dec. 24, 2019

(54) PISTON WASHER FOR A DRUG DELIVERY DEVICE AND DRUG DELIVERY DEVICE INCORPORATING SUCH PISTON WASHER

(71) Applicant: Novo Nordisk A/S, Bagsvaerd (DK)

(72) Inventors: Henrik Bengtsson, Taastrup (DK); Ronan Carroll, Tisvildeleje (DK); Soeren Steenfeldt-Jensen, Hornbaek (DK); Henning Graaskov, Bagsvaerd (DK); Jan Harald Preuthun, Broenshoej (DK); Emil Gram Spork, Copenhagen N (DK)

(73) Assignee: Novo Nordisk A/S, Bagsvaerd (DK)

( * ) Notice: Subject to any disclaimer, the term of this patent is extended or adjusted under 35 U.S.C. 154(b) by 157 days.

(21) Appl. No.: 15/735,943

(22) PCT Filed: Jul. 1, 2016

(86) PCT No.: PCT/EP2016/065620
§ 371 (c)(1),
(2) Date: Dec. 12, 2017

(87) PCT Pub. No.: WO2017/001693
PCT Pub. Date: Jan. 5, 2017

(65) Prior Publication Data
US 2018/0177952 A1  Jun. 28, 2018

(30) Foreign Application Priority Data

Jul. 1, 2015 (EP) .................................... 15174922

(51) Int. Cl.
*A61M 5/315* (2006.01)
*A61M 5/24* (2006.01)
*A61M 5/20* (2006.01)

(52) U.S. Cl.
CPC .......... *A61M 5/31515* (2013.01); *A61M 5/24* (2013.01); *A61M 5/3155* (2013.01);
(Continued)

(58) Field of Classification Search
CPC .. A61M 5/24; A61M 5/2033; A61M 5/31551; A61M 5/20; A61M 5/31553;
(Continued)

(56) References Cited

U.S. PATENT DOCUMENTS 9,138,543 B2  9/2015 Frantz et al.
2010/0280461 A1*  11/2010 Forstreuter ....... A61M 5/31515
  604/228

FOREIGN PATENT DOCUMENTS

WO  9938554 A1  8/1999
WO  200119434 A1  3/2001
(Continued)

*Primary Examiner* — Manuel A Mendez
(74) *Attorney, Agent, or Firm* — Wesley Nicolas (57) ABSTRACT

The present invention relates to a piston washer (109, 209) for use in a drug delivery device for transferring a distally directed axial force from a piston rod (107, 207) towards a piston (199, 299) of a held cartridge (189, 289). The piston washer (109, 209) defines a proximal surface portion (109a) adapted for engagement with the distal portion of a piston rod (107, 207) and a distal surface portion (109b) configured to engage and abut a piston (199, 299). An axial distance defining device (19a1, 109b1, 109c, 209c) is positioned between the proximal surface portion (109a) and the distal surface portion (109b), wherein the axial distance defining device (19a1, 109b1, 109c, 209c) is configured to be shifted from a first axial compressible state into a second axial non-compressible state. The invention further relates to a drug delivery device incorporating such piston washer (109, 209).

12 Claims, 3 Drawing Sheets

(52) U.S. Cl.
CPC .... *A61M 5/31541* (2013.01); *A61M 5/31551* (2013.01); *A61M 5/31581* (2013.01); *A61M 5/31591* (2013.01); *A61M 5/31593* (2013.01); *A61M 5/2033* (2013.01); *A61M 2207/00* (2013.01)

(58) Field of Classification Search
CPC ............ A61M 5/2448; A61M 5/31541; A61M 5/31511; A61M 5/3158; A61M 5/31585; A61M 5/31568; A61M 5/3202; A61M 5/31535; A61M 5/19; A61M 5/31543; A61M 5/3157; A61M 5/30; A61M 5/31536; A61M 5/31583; A61M 5/315
See application file for complete search history.

(56) References Cited

FOREIGN PATENT DOCUMENTS

| | | |
|---|---|---|
| WO | 2006/128794 A2 | 12/2006 |
| WO | 2007/017052 A1 | 2/2007 |
| WO | 2009095332 A1 | 8/2009 |
| WO | 2010/124961 A1 | 11/2010 |
| WO | 2010/139634 A1 | 12/2010 |
| WO | 2010149209 A1 | 12/2010 |
| WO | 2013156224 A1 | 10/2013 |

* cited by examiner

Prior art

Fig. 2

Prior art

PISTON WASHER FOR A DRUG DELIVERY DEVICE AND DRUG DELIVERY DEVICE INCORPORATING SUCH PISTON WASHER

CROSS-REFERENCE TO RELATED APPLICATIONS

This application is a 35 U.S.C. § 371 National Stage application of International Application PCT/EP2016/065620 (published as WO 2017/001693), filed Jul. 1, 2016, which claims priority to European Patent Application 15174922.3, filed Jul. 1, 2015; the contents of which are incorporated herein by reference.

The present invention relates to an assembly of components for a drug delivery device that allows a user to select single or multiple doses of an injectable liquid drug and to dispense the set dose of the product and to apply said product to a patient, preferably by injection. In particular, the present invention relates to a method of assembling such drug delivery devices.

BACKGROUND

In the disclosure of the present invention reference is mostly made to drug delivery devices used e.g. in the treatment of diabetes by delivery of insulin, however, this is only an exemplary use of the present invention.

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe. Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the liquid drug to be administered is provided in a cartridge that has a moveable piston or bung mechanically interacting with a piston rod of an expelling mechanism of the drug delivery device. By applying thrust to the piston in distal direction, a predefined amount of the liquid drug is expelled from the cartridge. Due to inevitable manufacturing tolerances there may for instance persist axial clearance between a cartridge's piston and the piston rod. Typically, prior to a primary use of the device, an end-user has to conduct a so-called priming of the expelling mechanism in order to ensure, that already with an initial dose setting and a first subsequent dose dispensing step, an accurate amount of the liquid drug is dispensed in a predefined way.

An initial dose setting and expelling of a minor dose may in certain situations also be required for removing any air present in the cartridge and/or a connected needle and for performing a flow check.

Document WO 99/38554 A1 discloses several embodiments of injection devices each suitable for forming a disposable device wherein a liquid drug cartridge is inserted into the device during assembly in a production line.

State of the art pen-type drug delivery devices that incorporate a dose setting feature often include a so-called end-of-content limiter to prevent a user from selecting a size of a dose which exceeds the amount of liquid drug remaining in a cartridge of the device. References WO 01/19434 A1, WO 2006/128794 A2, WO 2010/149209 A1, WO 2007/017052 A1 and WO 2013/156224 A1 include disclosure of such end-of-content limiters.

In the production line, during final assembly operations of the devices, at least a part of the priming is typically carried out using the dose setting and expelling mechanism so that users will experience virtually consistent requirement for a priming operation across individual pen samples irrespective of the initial gap between the piston rod and the piston which emanates from tolerances. Reference WO 2009/095332 A1 discloses devices wherein a distance between the distal end of a piston rod means and the plunger is minimized or reduced to zero.

SUMMARY

It is an object of the present invention to provide a drug delivery device featuring improved and facilitated clearance reduction or clearance elimination. It is a further object of the invention to provide a simplified and robust method of eliminating clearance in a drug delivery device. Finally, it is an object of the invention to provide manufacture of drug delivery devices providing consistently uniform and predictable total doseable amount of liquid drug from a held cartridge.

In the disclosure of the present invention, embodiments and aspects will be described which will address one or more of the above objects or which will address objects apparent from the below disclosure as well as from the description of exemplary embodiments.

In a first aspect, the present invention relates to a piston washer for use in a drug delivery device for transferring a distally directed axial force from a piston rod towards a piston of a held cartridge is provided. The piston washer defines:

a proximal surface portion adapted for engagement with the distal portion of a piston rod,
  a distal surface portion configured to engage and abut a piston of a held cartridge, and
  an axial distance defining device positioned between the proximal surface portion and the distal surface portion, wherein the distance defining device is configured to be shifted from a first axial compressible state into a second axial non-compressible state wherein:
  in the first axial compressible state the distance defining device allows the distal surface portion and the proximal surface portion to be moved relative towards each other upon exertion of an externally applied axial compression force, and
  in the second axial non-compressible state prevent relative axial movement between the distal surface portion and the proximal surface portion.

A piston washer according to the first aspect may be used in a drug delivery device for eliminating clearance between the piston rod and the piston of a held cartridge so that the piston washer automatically adapts to the initial clearance provided between the piston rod and the piston of a held cartridge as the drug delivery device is assembled.

In some embodiments, during assembly of a drug delivery device, after the piston rod and the piston of a held cartridge has been brought into their intended positions, the distance defining device is shifted from the first compressible state and into a second non-compressible state. Subsequent to the distance defining device is shifted from the first compressible state and into a second non-compressible state, relative axial movement between the distal surface portion and the proximal surface portion is prevented, and the piston washer is subsequently able to transfer axial forces from the piston rod towards the piston of the held cartridge for expelling one or more doses from the drug delivery device. Hence, the initial clearance between the piston rod and the piston may be effectively eliminated.

The piston washer may be configured for having a non-compressed configuration having an initial axial dimension between the distal surface portion and the proximal surface portion and be reconfigurable into a compressed configuration having a reduced axial dimension shorter than the initial axial dimension.

Exemplary piston washer axial dimensions before compression may be selected in the range of 1.5 mm to 5 mm, preferably 2.0 mm to 3.0 mm more preferably in the range 2.1 mm to 2.7 mm.

The piston washer may be configured for being loosely withheld between the piston rod of the drug delivery device and the piston of a held cartridge. Hence, when the piston washer assumes its final configuration, the piston washer will be able to rotate independently from a rotating piston rod, i.e. allowing the piston washer to be kept non-rotatable while the piston rod rotates, e.g. during dose expelling.

A proximal rigid shell may define the proximal surface portion. A distal rigid shell may define the distal surface portion.

In some embodiments a proximal rigid shell defines the proximal surface portion and an axial and circumferentially extending first surface wall. A distal rigid shell defines the distal surface portion and defines an axial and circumferentially extending second surface wall. The first surface wall and the second surface wall are configured for being telescopically moved relative to each other when the distance defining device assumes the first axial compressible state.

In some forms the proximal rigid shell and the distal rigid shell together form a receptacle.

In some embodiments, when the axial distance defining device is in the first axially compressible state, the piston washer may be configured to provide reluctance against relative axial movement between the distal rigid shell and the proximal rigid shell by cooperating surfaces of the first surface wall and the second surface wall.

When the distance defining device is in the first axial compressible state the first surface wall and the second surface wall are axially movable relative to each other. In some embodiments, the piston washer is so configured that the force required for axially moving the first surface wall and the second surface wall relative to each other is smaller than the break-loose force required for moving the piston in the cartridge. In other embodiments said force required for axially moving the first surface wall and the second surface wall relative to each other is less than 70% of the break-loose force, such as less than 50% of the break-loose force, such as smaller than 30% of the break-loose force.

By securing the first surface wall and the second surface wall relative to each other this causes the distance defining device to assume the second axial non-compressible state. The shift from the first axial compressible state and into the second axial non-compressible state may be permanent and thus irreversible.

In some embodiments, the proximal rigid shell and the distal rigid shell are adhered relative to each other. In further embodiments, a portion of an adhesive is arranged between the first surface wall and the second surface wall. When the distal surface portion and the proximal surface portion are positioned relative to each other in a desired target position the adhesive is cured causing the distance defining device to shift into the second axial non-compressible state.

In other embodiments the proximal rigid shell and the distal rigid shell are joined by one or more of the processes of the group comprising ultrasonic welding, laser radiation and induction welding to cause the distance defining device to shift into the second axial non-compressible state.

In some forms a spring device is arranged between the distal surface portion and the proximal surface portion, said spring device providing a biasing force for moving the distal surface portion axially away from the proximal surface portion and being arranged for being axially compressed upon exertion of an externally applied axial compression force when the distance defining device assumes the first axial compressible state.

The distance defining device comprises an amount of a polymeric substance arranged between the distal surface portion and the proximal surface portion. The polymeric substance assumes a liquefied high viscosity state when the distance defining device is in the first compressible state to allow the polymeric substance to shift from a shape having an initial axial dimension into a shape having a reduced axial dimension shorter than the initial axial dimension. The polymeric substance is curable causing the distance defining device to shift into the second axial non-compressible state to maintain the shape having the reduced axial dimension.

In a second aspect, the present invention relates to a drug delivery device incorporating a piston washer in accordance with the first aspect.

Such drug delivery device may be configured for expelling a dose of drug from a held cartridge, the drug delivery device defining a distal drug outlet end and an opposite proximal end and comprising:
  a housing component holding a cartridge comprising a liquid drug and a piston slideable arranged therein in an axial direction,
  a dose setting and expelling mechanism comprising a piston rod for exerting a force on the piston of the cartridge in a distal direction for expelling a dose, wherein the piston washer is arranged axially between the piston of the cartridge and the piston rod.

In some embodiments the piston washer is arranged non-attached with respect to the piston rod and/or non-attached with respect to the piston of the held cartridge. However, after assembly of the device, the piston washer is arranged with the distal surface portion in abutting contact with the piston and the proximal surface portion in abutting contact with the piston rod.

In some embodiments, the piston rod is configured to rotate during dose expelling. In one embodiment, the piston washer is rotatably arranged relative to the piston rod to allow the piston rod to rotate while the piston washer remains non-rotatable.

The dose setting and expelling mechanism may comprise a dose setting element that rotates relative to a driver during setting of a dose and wherein the dose setting element and the driver rotates together during expelling of a set dose.

In a third aspect of the invention the drug delivery device according to the second aspect comprises an end-of-content limiter which prevents setting a dose which exceeds a doseable amount of liquid drug remaining in the cartridge.

The end-of-content limiter may in some embodiments be arranged between the driver and the dose setting element of the drug delivery device. In exemplary embodiments the end-of-content limiter is engaging the driver and the dose setting element. In such embodiment, as the dose setting element is rotated relative to the driver for dialling up a dose, the end-of-content limiter moves towards an end-of-content stop geometry for example provided by one of the driver and the dose setting element. In other embodiments, the end-of-content limiter is engaging the piston rod and a dose setting element. In such embodiment, as the dose setting element is rotated relative to the piston rod for dialling up a dose, the end-of-content limiter moves towards an end-of-content stop geometry for example provided by one of the piston rod and the dose setting element.

In a fourth aspect, the invention relates to a method of preparing a piston washer for use in a drug delivery device for transferring a distally directed axial force from a piston rod towards a piston of a held cartridge. The method of preparing the piston washer comprises the steps of:

a1) providing a proximal surface portion adapted for engagement with the distal portion of a piston rod of a drug delivery device, a2) providing a distal surface portion configured to engage and abut a piston of a cartridge held by a drug delivery device, a3) providing an axial distance defining device to be arranged between the proximal surface portion and the distal surface portion, wherein the axial distance defining device is configured to be shifted from a first axial compressible state and into a second axial non-compressible state, b1) arranging the proximal surface portion, the distal surface portion and the axial distance defining device positioned between the proximal surface portion and the distal surface portion, b2) with the axial distance defining device in the first axial compressible state, by applying an externally applied axial compression force moving the distal surface portion and the proximal surface portion axially towards each other until the distal surface portion and the proximal surface portion are positioned relative to each other in a desired target position, and c1) shifting the axial distance defining device from the first axial compressible state to the second axial non-compressible state to prevent relative axial movement between the distal surface portion and the proximal surface portion.

In some embodiments, the steps b2) and b3) are performed during assembly of a drug delivery device, wherein the proximal surface portion and the distal surface portion are positioned between the piston rod of an expelling mechanism of the drug delivery device and the piston of a held cartridge.

In particular embodiments, the step b2) is performed by moving the piston rod and the cartridge axially towards each other. In exemplary embodiments, the piston rod and the cartridge are moved axially towards each other by relatively moving a housing component of the drug delivery device and the cartridge.

In particular forms, the method according to the fourth aspect relates to a method of eliminating clearance between a piston and a piston rod of a drug delivery device during assembly thereof wherein said externally applied axial compression force is exerted by the piston rod and a piston of a the cartridge of the drug delivery device during assembly thereof.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF DRAWINGS

In the following the invention will be further described with reference to the drawings, wherein.

Generally, in the figures, like structures are mainly identified by like reference numerals, e.g. so that parts carrying reference no. "7" in FIG. 1 correspond to reference no. "107" in FIGS. 3a through 4b, and correspond to reference no. "207" in FIGS. 5a-5b, respectively.

DESCRIPTION

The shown figures are schematic representations for which reason the configuration of the different structures as well as their relative dimensions are intended to serve illustrative purposes only. In the following, when the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1:
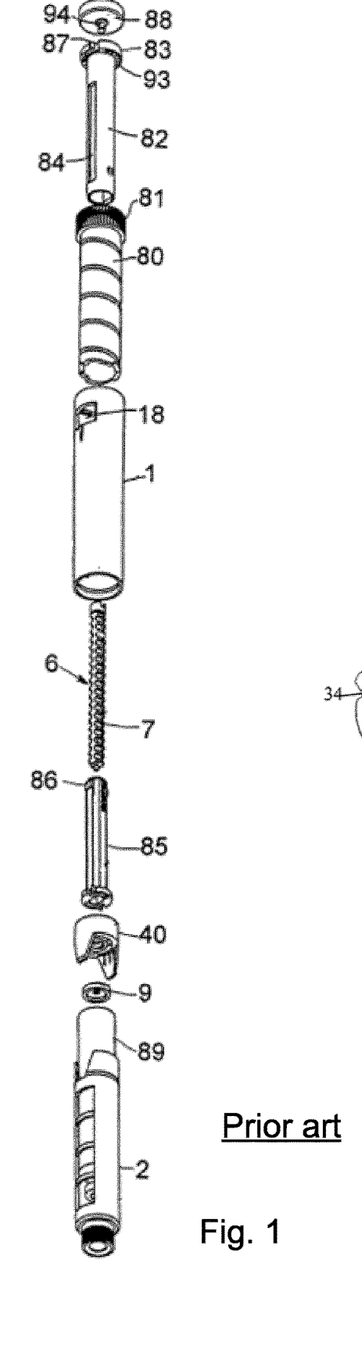
FIG. 1 shows a prior art injection device in an exploded view showing the various components.

Shown in FIG. 1 is an exploded view of components of a prior art pen-formed drug delivery device as disclosed in connection with FIG. 15-17 of reference WO 99/38554 A1. FIG. 1 of the present disclosure is a reproduction of FIG. 17 of that reference. In the present context the device represents a "generic" prior art drug delivery device providing an example of an injection pen, e.g. a pen shaped injection device which may define a central longitudinal axis along which a piston of a held cartridge is arranged for slideable movement. The injection device is provided with a dose setting and expelling mechanism for setting and expelling one or more doses of a drug, e.g. operable for selecting the size of a dose in a dose setting procedure and expelling the set dose during a dose expelling procedure. A drug delivery device closely related to the device shown in FIG. 1 is marketed by Novo Nordisk as NovoPen FlexPen®.

More specifically, the pen device shown in FIG. 1 comprises a cap part (not shown) and a main part having a proximal body or drive assembly portion with a proximal housing component 1 in which a drug expelling mechanism is arranged or integrated, and a distal housing component 2 forming a cartridge holder portion in which a drug-filled transparent cartridge 89 (with a non-referenced distal needle-penetrable septum) can be arranged and retained in place. The distal end of the distal housing component 2 thus forms a drug outlet.

Only components directly necessary for the understanding of the present disclosure will be described herein. For the full description of the expelling mechanism reference is made to WO 99/38554 A1 which is hereby incorporated by reference.

In the fully assembled state, the distal housing component 2 is fixedly attached to the proximal housing component 1, e.g. by an axial snap connection, the distal housing component 2 having openings allowing a portion of the cartridge 89 to be inspected. The cartridge may for example contain an insulin, GLP-1 or growth hormone formulation. The device is designed to irreplaceably accommodate a cartridge 89 inserted through a proximal receiving opening in the distal housing component 2, the cartridge being provided with a piston driveable by a piston rod forming part of the expelling mechanism. A piston washer 9 may be located between the piston rod and the piston for transferring axial forces exerted by the piston rod to the piston.

Again referring to FIG. 1, a nut element 40 is fixedly secured to the distal housing component 2 at a predefined axial location thereof. The nut element 40 defines a central opening extending a along a central axis of the injection device, the opening defining an inner thread. A piston rod 7 includes an outer thread adapted to engage the inner thread of the nut element 40. The piston rod 7 further includes a longitudinal recessed track 6, a pair of flattened surfaces or similar longitudinal extending geometry for cooperating with a mating geometry of a driver tube 85 of the expelling mechanism to enable relative axial movement between the piston rod 7 and the driver tube 85 but prevent relative rotation. In the shown embodiment, the driver tube 85 is part of a multi-piece driver comprising driver tube 85 and bushing 82. Driver tube 85 and bushing 82 are configured for rotating together but to be axially displaceable relative to each other. Driver tube 85 is mounted for rotation at an axially fixed location with respect to proximal housing component 1. Driver tube 85 is rotated during dose expelling but remains non-rotatable during dose setting. A dose setting element formed as a scale drum 80 is mounted in a thread of the proximal housing component 1 and arranged to encircle and axially overlap bushing 82. During dose setting the scale drum 80 is dialled up by rotating in the thread of proximal housing component 1. Scale drum 80 is thus moved in a proximal direction relative to the proximal housing component 1 to extend proximally a distance proportional to the size of the set dose. During this dose setting procedure, the bushing 82 is moved along axially but bushing is prevented from rotating relative to the housing. A set dose is expelled by a user forcing an injection button 88 in the distal direction. During this, the scale drum 80 is rotated back towards an initial position. The bushing 82 is coupled to the scale drum 80 so that it rotates with the scale drum 80 during injection. The driver tube 85 is forced to rotate as well and acts to rotate the piston rod 7 through the nut element 40. In accordance herewith the piston rod 7 transfers a force in the distal direction forcing the piston of the cartridge 89 to move distally for expelling a quantity equal to size of the set dose.

Particular variants of the injection pen shown in FIG. 1 may include a dose setting limiter which prevents setting of a dose exceeding the doseable amount of liquid drug remaining in the cartridge of the injection device. One suitable dose setting limiter, i.e. a so-called "end-of-content limiter" is disclosed and shown in FIG. 3 of WO 01/19434 A1, and further reproduced in the present disclosure in FIG. 2. In the embodiment shown, the driver 31 forms an element generally corresponding to the driver of the device shown in FIG. 1, i.e. bushing 82. An outer helical track 33 is disposed on the driver 31. A dose setting limiter is defined by nut member 32 which is threadedly coupled to helical track 33 of driver 31. Further, in FIG. 2, a dose setting element 30 corresponds to the scale drum 80 of FIG. 1. At its outer wall the nut member 32 is in the axial direction provided with a recess 34 which is engaged by a ridge 35 in the axial direction on the inner side of the dose setting element 30.

Figure 2:
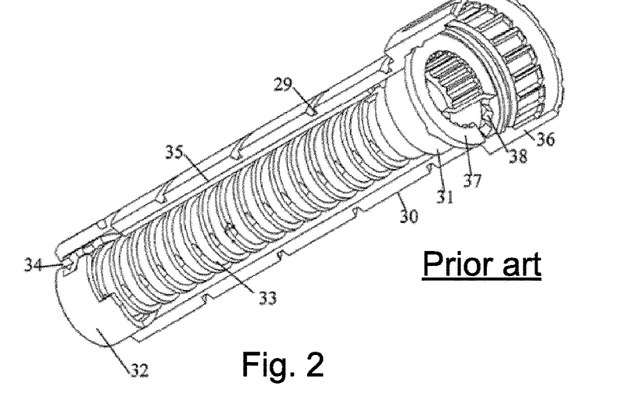
FIG. 2 shows schematically a prior art end-of-content limiter suitable for incorporation in an injection device similar to the one shown in FIG. 1.

The helical track has a length which correlates with the total amount of drug in a new full cartridge. During dose setting the driver 31 remains non-rotatable while the dose setting element 30 rotates. Hence, when dialling up a dose the nut member 32 moves towards an end stop of helical track 33. During dose expelling the driver 31 rotates with the dose setting element 30. Hence nut member 32 maintains its present position relative to helical track 33. The nut member 32 only abuts the end stop of the helical thread 33 when the sum of accumulated expelled doses and the present set dose equals the total amount of liquid drug in a full cartridge. This prevents setting a dose that exceeds the amount of liquid drug remaining in the cartridge.

The shown end-of-content limiter provides only a non-limiting example of a suitable end-of-content limiter to be used in connection with the injection device shown in FIG. 1. Other known end-of-content limiters may alternatively be used in the injection device, such as the end-of-content limiters disclosed in WO 2006/128794 A2, WO 2010/149209 A1, WO 2007/017052 A1, and WO 2013/156224 A1. In accordance with such end-of content mechanisms, instead of an end-of-content limiter formed as a nut member as such, a corresponding track follower that does not necessarily be formed as a "nut" may be used instead, where the track follower may include a first track coupling being coupled to a driver and a second track coupling being coupled to a dose setting element. When used in the present disclosure, the term "nut member" and "end-of-content limiter" will encompass any type of end-of-content limiter.

In accordance with the assembling procedure of the prior art injection device shown in FIG. 1, the device may be assembled by forming a distal subassembly which includes distal housing component 2, cartridge 89, piston washer 9, nut element 40 and piston rod 7. In distal subassembly, the nut element 40 is secured relative to the distal housing component 2 at a particular predefined axial position by means of an axial snap fit. The piston rod 7 is provided in an already threadedly engaged state relative to nut element 40 where the piston rod 7 assumes a particular rotational orientation relative to distal housing component 2 and where the distal end of the piston rod is in close proximity with the piston washer 9, the piston washer being located adjacent the piston of cartridge 89.

The proximal subassembly includes the remaining components of the injection device, i.e. the proximal subassembly includes the proximal housing component 1 and the dose setting and expelling mechanism in a state where the nut member 32 assumes a pre-defined start position relative to the helical track of the driver (i.e. bushing 82) and where the driver tube 85 assumes a predefined rotational orientation relative to the proximal housing component 1. This allows the piston rod 7 to slide into engagement with the driver tube 85 as the distal subassembly is axially brought into engagement with the proximal subassembly for finally securing the two subassemblies relative to each other, this without requiring relative rotation between piston rod 7 and driver tube 85.

Production tolerances on the piston rod, the dose setting and expelling mechanism, cartridge body, cartridge filling level and other components result in variations in piston rod position and piston position in each device during assembly.

In mechanical devices production, in order to minimize a potential clearance between the piston rod and the piston of the cartridge, positioning may be carried out by initially positioning the piston rod 7 in a nominal position. Due to tolerances various different clearance gaps between the piston and the piston rod will show when the distal and proximal subassemblies of each sample are permanently secured together. On the basis of measurements or estimations, which may be performed at different steps of the assembly process, the actual gap in each sample traditionally has been eliminated or at least partly reduced by operating the dose setting and expelling mechanism. Operating the dose setting and expelling mechanism may be carried out either after final assembly or prior to final assembly of the different subassemblies. However such compensation procedure means that the end-of-content mechanism will be operated to a lesser or higher degree even before the device is shipped to the user meaning that the experienced total doseable volume varies from sample to sample. Generally such variations and inconsistencies from one sample to another should be avoided as this may provide the impression that the quality of the device could be somewhat non-optimal.

Figure 3A:
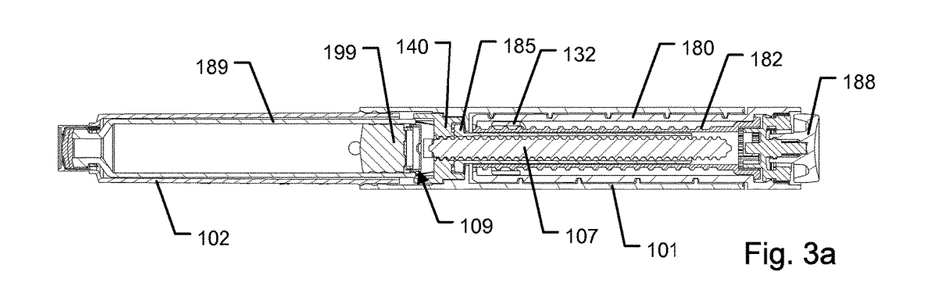
FIG. 3a shows a cross sectional view of an exemplary embodiment injection device having a piston washer according to a first embodiment arranged for abutting the piston in a state prior to final assembly.
Figure 3B:
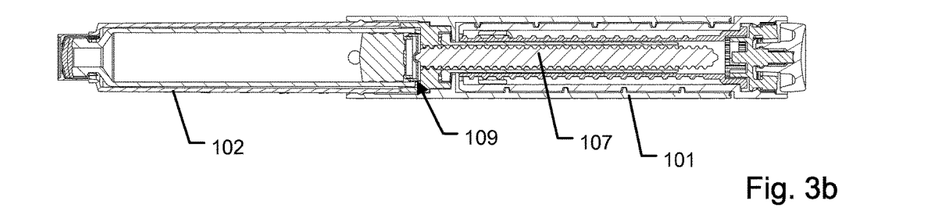
FIG. 3b shows a cross sectional view of the device of FIG. 3a in a state after final assembly.
Figure 4A:
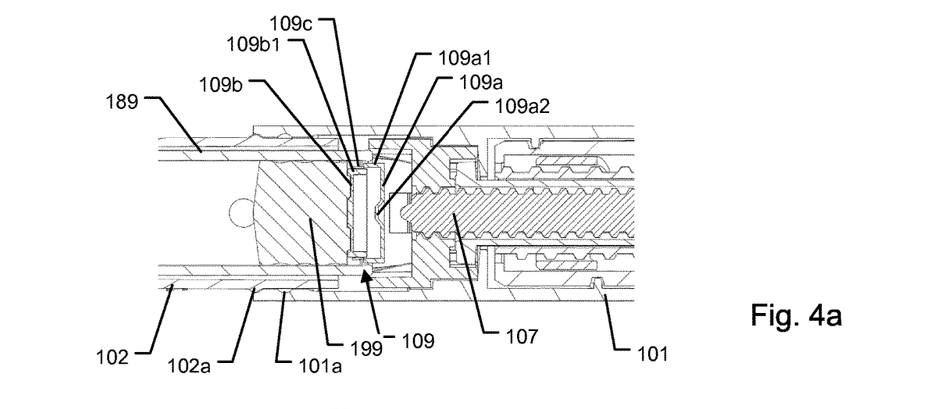
FIG. 4a is a detailed view of the piston washer configuration shown in FIG. 3a, FIG. 4b is a detailed view of the piston washer configuration shown in FIG. 3b.
Figure 4B:
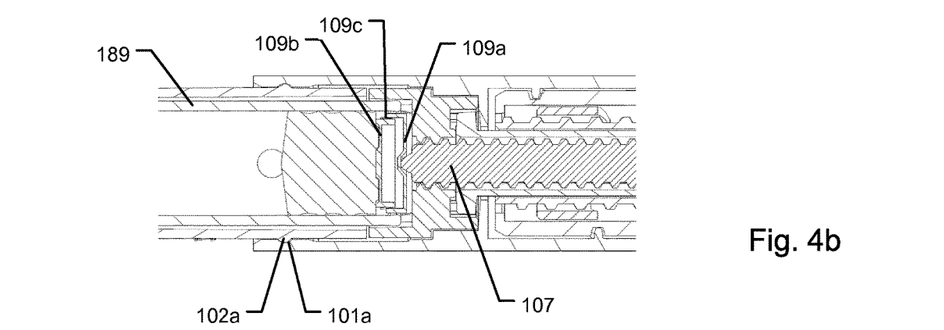

Turning now to FIGS. 3a and 3b a first embodiment of an improved drug delivery device and an associated assembly method will now be described. In FIGS. 3a and 3b an improved piston washer 109 according to a first embodiment is shown. FIGS. 4a and 4b provide an enlarged view of components located around piston washer 109. Piston washer 109 includes a proximal surface portion formed by a proximal rigid shell 109a configured for engaging the distal end of piston rod 107. Piston washer 109 further comprises a distal surface portion formed by a distal rigid shell 109a configured for engaging and abutting the proximal end face of piston 199 of a held cartridge 189.

The proximal rigid shell 109a defines an axial and circumferentially extending first surface wall 109a1. The distal rigid shell 109b defines an axial and circumferentially extending second surface wall 109b1. In the shown embodiment both the first surface wall and the second surface wall are formed as tubular wall elements. The first surface wall 109a1 and the second surface wall 109b1 are configured for being telescopically moved relative to each other. In the shown embodiment, the proximal rigid shell and the distal rigid shell together form a receptacle.

The improved piston washer 109 includes an axial distance defining device positioned between the proximal surface portion and the distal surface portion. The axial distance defining device is configured to be shifted from a first axial compressible state into a second axial non-compressible state. In the first axial compressible state the axial distance defining device allows the distal surface portion and the proximal surface portion to be moved relative towards each other upon exertion of an externally applied axial compression force. In a second axial non-compressible state the axial distance defining device prevents relative axial movement between the distal surface portion and the proximal surface portion.

The improved piston washer 109 initially has a first configuration having an initial axial dimension of relatively large axial length. The piston washer may be compressed into a second configuration having a reduced axial dimension by exerting an axial compressive force urging the proximal rigid shell 109a and the distal rigid shell 109b axially towards each other. The first surface wall 109a1 and the second surface wall 109b1 are configured for being telescopically moved relative to each other if the reluctance against moving is overcome.

An amount of an adhesive 109c is arranged between the first surface wall 109a1 and the second surface wall 109b1. In FIGS. 3a and 4a, the adhesive is not yet cured allowing the proximal rigid shell 109a and the distal rigid shell 109b to be axially moved towards each other.

When assembling the distal subassembly relative to the proximal subassembly by moving the two subassemblies axially together the piston washer 109 will at some point become squeezed between the piston rod 107 and the piston 199. As the two subassemblies are brought axially closer together the axial dimension of the piston washer 109 will diminish. This continues until snap elements of the distal housing component 102a snaps into engagement with the cooperating snap elements of the proximal housing component 101a. This is shown in FIGS. 3b and 4b. The axial dimension of the piston washer 109 will now have become adapted to the gap that would exist between the piston rod and the piston if the piston washer 109 was absent.

After the state shown in FIGS. 3b and 4b has been established, the adhesive 109c will become cured for fixation of the proximal rigid shell 109a and the distal rigid shell 109b relative to each other. Curing of the adhesive may be carried out by any known method. Non-limiting examples include curing by application of heat, radiation, such as UV radiation, or any other principles known in the art.

Alternatively or in addition to joining the proximal rigid shell 109a and the distal rigid shell 109b relative to each other by using an adhesive, the two parts may be secured by other means such as laser radiation, ultrasonic welding or similar fastening process. To facilitate application of radiation towards the piston washer 109, such as for curing the adhesive 109c, one or more openings in the housing of the injection device may be provided (not shown).

In the shown embodiment, the nut element 140 is attached to proximal housing component 101. In other embodiments, the nut element 140 may be attached to distal housing component 102 before the distal housing component 102 is attached to proximal housing component 101.

A further not shown embodiment which resembles the design shown in FIGS. 3a through 4b further incorporate a spring device being arranged between the distal surface portion and the proximal surface portion of the piston washer. The spring device is configured for providing a biasing force acting to urge the distal surface portion axially away from the proximal surface portion. The spring device may be provided as a compression spring, a foam element or any other element suitable for providing said biasing force. When the distance defining device assumes the first axial compressible state, upon exertion of an externally applied axial compression force, the distal surface portion and the proximal surface portion will be moved axially towards each against the force urged by the spring device. When a desired axial target dimension of the piston washer has been obtained the proximal rigid shell and the distal rigid shell are secured relative to each other.

Figure 5A:
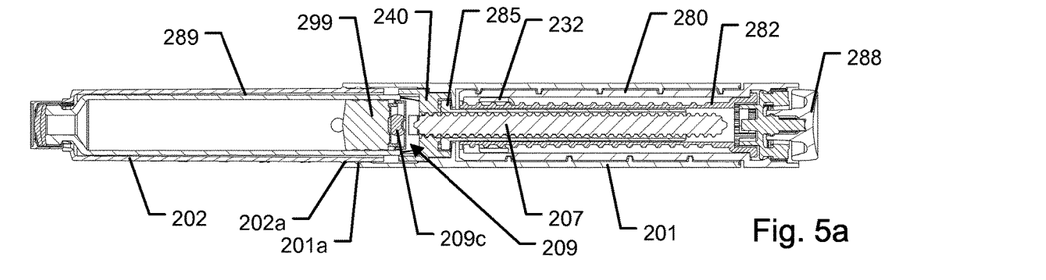
FIG. 5a shows a cross sectional view of an exemplary embodiment injection device having a piston washer according to a second embodiment arranged for abutting the piston in a state prior to final assembly.
Figure 5B:
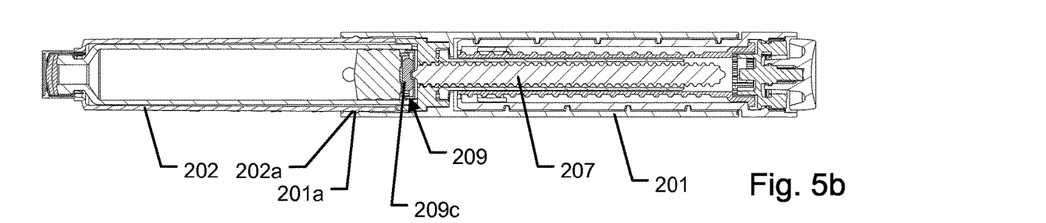
FIG. 5b shows a cross sectional view of the device of FIG. 5a in a state after final assembly.

FIGS. 5a and 5b show a second embodiment of an improved drug delivery device and an associated assembly method will now be described. The figures show an injection device that incorporates an improved piston washer 209 according to a second embodiment FIGS. 5a and 5b show a second embodiment of an improved drug delivery device and an associated assembly method will now be described. The FIGS. 5a and 5b show an injection device that incorporates an improved piston washer 209 according to a second embodiment.

The piston washer 209 again includes a proximal surface portion formed by a proximal rigid shell configured for engaging the distal end of piston rod 207. Piston washer 209 further comprises a distal surface portion formed by a distal rigid shell configured for engaging and abutting the proximal end face of piston 299 of a held cartridge 289. The proximal rigid shell and the distal rigid shell may generally be formed similar to the corresponding parts shown in FIGS. 4a and 4b. In the shown embodiment, the piston washer 209 forms a receptacle having a hollow interior space.

Inside the space of the piston washer 209 an amount of a curable polymeric paste is arranged. In the shown embodiment, prior to curing, the polymeric substance assumes a liquefied high viscosity state in the state shown in FIGS. 5a and 5b.

When assembling the distal subassembly relative to the proximal subassembly by moving the two subassemblies axially together the piston washer 209 will at some point become squeezed between the piston rod 207 and the piston 299. As the two subassemblies are brought axially closer together the axial dimension of the piston washer 209 will diminish. This continues until snap elements of the distal housing component 202a snaps into engagement with the cooperating snap elements of the proximal housing component 201a. This is shown in FIG. 5b. The axial dimension of the piston washer 209 will now have become adapted to the gap that would exist between the piston rod and the piston if the piston washer 209 was absent.

During compression of the piston washer 209 the polymeric substance shifts from a shape having an initial axial dimension into a shape having a reduced axial dimension shorter than the initial axial dimension, compare FIG. 5a and FIG. 5b.

After the state shown in FIG. 5b has been established, the curable polymer paste will become cured for preventing further axial compression between the proximal rigid shell and the distal rigid shell. Curing of the polymer paste may be carried out by any known method. Non-limiting examples include curing by application of heat, radiation, such as UV radiation, or any other principles known in the art.

The above described methods may include a "standard dose setting and expelling procedure" to be performed either before the state shown in FIG. 3a, 5a or subsequent to the state shown in FIG. 3b, 5b. The "standard dose setting and expelling procedure" may be the same across the individual devices of the production line. Such dose setting and expelling procedure may for example be carried out for performing a function check for the dose setting and expelling mechanism.

The assembly methods have been provided so that the distal housing component and the proximal housing component has a proper rotational orientation relative to each other so that the intended rotational alignment between a window opening for the scale drum with the inspection openings of the cartridge holder is ensured. The assembled injection device is now ready for labelling and other subsequent finalization steps.

By using the described design of embodiment 1 and 2 and their respective assembly methods, the clearance of each individual pen device can be effectively eliminated between individual pen devices. In situations where and end-of-content mechanism is incorporated into the device, the pen manufacturing and assembly can be carried out without use of the dose setting and expelling mechanism for evening out the gap between the piston rod and the piston and thus further enables the end-of-content mechanism of each individual device to provide a consistent and uniform total doseable quantity from each individual pen device.

For a non-limiting exemplary piston washer the axial dimension in the non-compressed state may be selected in the order of 2.0 mm to 3.0 mm such as 2.7 mm where the axial dimension corresponds to the axial distance from the most distal point of the piston rod and to the most proximal point of the piston when these component both engages the piston washer when initiating compression of the piston washer.

The injection device shown in FIG. 1 provides a non-limiting example of a manual pen injector where the expelling mechanism is fully manual in which case the dose setting element and the injection button moves proximally during dose setting corresponding to the set dose size, and then is moved distally by the user to expel the set dose, this corresponding to the shown embodiments.

In alternative embodiments of injection devices these may incorporate an energy storage aiding to expel a set dose when a user operates a dose injection button. Depending on the type of expelling mechanism embodied in a given drug delivery device, the expelling mechanism may comprise a spring which is strained during dose setting and then released to drive the piston rod when the release button is actuated. Still other alternative mechanisms may include a spring member which stores sufficient energy for expelling the total contents of a cartridge during one or more separate dose administrations. Each such types of injection devices can be structured to enable assembly by the above described methods and features in accordance with the different aspects of the present invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A piston washer for use in a drug delivery device for transferring a distally directed axial force from a piston rod towards a piston of a held cartridge, the piston washer defining:
   a proximal surface portion adapted for engagement with the distal portion of a piston rod of the drug delivery device,
   a distal surface portion configured to engage and abut a piston of a held cartridge, and
   an axial distance defining device positioned between the proximal surface portion and the distal surface portions,
wherein the axial distance defining device is configured to be shifted from a first axial compressible state into a second axial non-compressible state wherein:

in the first axial compressible state the axial distance defining device allows the distal surface portion and the proximal surface portion to be moved relative towards each other upon exertion of an externally applied axial compression force, in the second axial non-compressible state prevents relative axial movement between the distal surface portion and the proximal surface portion, wherein the distance defining device comprises an amount of a polymeric substance arranged between the distal surface portion and the proximal surface portion, wherein the polymeric substance assumes a liquefied high viscosity state when the distance defining device is in the first axial compressible state to allow the polymeric substance to shift from a shape having an initial axial dimension into a shape having a reduced axial dimension shorter than the initial axial dimension, and wherein the polymeric substance is curable to maintain the shape having the reduced axial dimension causing the distance defining device to shift into the second axial non-compressible state.

2. A piston washer as defined in claim 1, wherein a proximal rigid shell defines the proximal surface portion.

3. A piston washer as defined in claim 1, wherein a distal rigid shell defines the distal surface portion.

4. A piston washer for use in a drug delivery device for transferring a distally directed axial force from a piston rod towards a piston of a held cartridge, the piston washer defining:

a proximal surface portion adapted for engagement with the distal portion of a piston rod of the drug delivery device, a distal surface portion configured to engage and abut a piston of a held cartridge, and an axial distance defining device positioned between the proximal surface portion and the distal surface portion, wherein the axial distance defining device is configured to be shifted from a first axial compressible state into a second axial non-compressible state wherein:

in the first axial compressible state the axial distance defining device allows the distal surface portion and the proximal surface portion to be moved relative towards each other upon exertion of an externally applied axial compression force, in the second axial non-compressible state prevents relative axial movement between the distal surface portion and the proximal surface portion, wherein a proximal rigid shell defines the proximal surface portion and an axial and circumferentially extending first surface wall, wherein a distal rigid shell defines the distal surface portion and a distal rigid shell portion defines an axial and circumferentially extending second surface wall, and wherein the first surface wall and the second surface wall are configured for being telescopically moved relative to each other when the axial distance defining device assumes the first axial compressible state.

5. A piston washer as defined in claim 4, wherein the proximal rigid shell and the distal rigid shell together form a receptacle.

6. A piston washer as defined in claim 4, wherein the piston washer, when the axial distance defining device assumes the first axially compressible state, is configured to provide a reluctance against relative axial movement between the distal rigid shell and the proximal rigid shell by cooperating surfaces of the first surface wall and the second surface wall.

7. A piston washer as defined in claim 4, wherein the first surface wall and the second surface wall are axially movable relative to each other when the distance defining device is in the first axial compressible state and wherein the first surface wall and the second surface wall are secured relative to each other to cause the distance defining device to assume the second axial non-compressible state.

8. A piston washer as defined in claim 7, wherein the proximal rigid shell and the distal rigid shell are adhered relative to each other.

9. A piston washer as defined in claim 7, wherein a portion of an adhesive is arranged between the first surface wall and the second surface wall, and wherein the adhesive is cured causing the distance defining device to shift into the second axial non-compressible state.

10. A piston washer as defined in claim 7, wherein the proximal rigid shell and the distal rigid shell are joined by one or more of the processes of the group comprising ultrasonic welding, laser radiation and induction welding.

11. A piston washer for use in a drug delivery device for transferring a distally directed axial force from a piston rod towards a piston of a held cartridge, the piston washer defining:

a proximal surface portion adapted for engagement with the distal portion of a piston rod of the drug delivery device, a distal surface portion configured to engage and abut a piston of a held cartridge, and an axial distance defining device positioned between the proximal surface portion and the distal surface portion, wherein the axial distance defining device is configured to be shifted from a first axial compressible state into a second axial non-compressible state wherein:

in the first axial compressible state the axial distance defining device allows the distal surface portion and the proximal surface portion to be moved relative towards each other upon exertion of an externally applied axial compression force, in the second axial non-compressible state prevents relative axial movement between the distal surface portion and the proximal surface portion, wherein a spring device is arranged between the distal surface portion and the proximal surface portion, said spring device providing a biasing force for moving the distal surface portion axially away from the proximal surface portion and being arranged for being axially compressed upon exertion of an externally applied axial compression force when the distance defining device assumes the first axial compressible state.

12. A drug delivery device for expelling a dose of drug from a held cartridge, the drug delivery device defining a distal drug outlet end and an opposite proximal end and comprising:

a housing component holding a cartridge comprising a liquid drug and a piston slideable arranged therein in an axial direction, a dose setting and expelling mechanism comprising a piston rod for exerting a force on the piston of the cartridge in a distal direction for expelling a dose, comprising a piston washer arranged axially between the piston of the cartridge and the piston rod for transferring a distally directed axial force from a piston rod towards a piston of a held cartridge, the piston washer defining:

a proximal surface portion adapted for engagement with the distal portion of a piston rod of the drug delivery device, a distal surface portion configured to engage and abut a piston of a held cartridge, and an axial distance defining device positioned between the proximal surface portion and the distal surface portion, wherein the axial distance defining device is configured to be shifted from a first axial compressible state into a second axial non-compressible state wherein:

in the first axial compressible state the axial distance defining device allows the distal surface portion and the proximal surface portion to be moved relative towards each other upon exertion of an externally applied axial compression force, in the second axial non-compressible state prevents relative axial movement between the distal surface portion and the proximal surface portion, and wherein the piston rod rotates during dose expelling and wherein the piston washer is rotatably arranged relative to the piston rod to allow the piston rod to rotate while the piston washer remains non-rotatable.

* * * * *